United States Patent [19]

Slusarchyk et al.

[11] Patent Number: 4,638,061

[45] Date of Patent: Jan. 20, 1987

[54] [3S(Z)]-2-[[[1-(2-AMINO-4-THIAZOLYL)-2-[[2,2-DIMETHYL-4-OXO-1-(SULFOOXY)-3-AZETIDINYL]AMINO]-2-OXOETHYLIDENE]-AMINO]OXY] ACETIC ACID AND INTERMEDIATE

[75] Inventors: William A. Slusarchyk, Belle Mead; William H. Koster, Pennington, both of N.J.

[73] Assignee: E. R. Squibb & Sons, Inc., Princeton, N.J.

[21] Appl. No.: 695,775

[22] Filed: Jan. 28, 1985

[51] Int. Cl.$^4$ .................. C07D 205/08; C07D 403/12
[52] U.S. Cl. ..................................... 540/355; 546/348
[58] Field of Search ......................... 260/239 A, 245.4

[56] References Cited

U.S. PATENT DOCUMENTS 4,337,197 6/1982 Gordon et al. ................. 260/239 A

FOREIGN PATENT DOCUMENTS 58-113174 7/1983 Japan .............................. 260/239 A
58-194856 11/1983 Japan .............................. 260/239 A
58-206589 12/1983 Japan .............................. 260/239 A

OTHER PUBLICATIONS

Shanzer et al, J. Org. Chem., 44: 3967 (1979).
Miller et al, J. Amer. Chem. Soc., 102: 7026 (1980).
Harding et al, J. Org. Chem., 46: 2809 (1981).
Floyd, J. Org. Chem., 47: 5160 (1982).
Slusarchyk et al, Heterocycles, 21: 191 (1984).

Primary Examiner—Mark L. Berch
Attorney, Agent, or Firm—Lawrence S. Levinson; Donald J. Barrack

[57] ABSTRACT

Pharmaceutically acceptable salts of [3S(Z)]-2-[[[1-(2-amino-4-thiazolyl)-2-[[2,2-dimethyl-4-oxo-1-(sulfooxy)-3-azetidinyl]amino]-2-oxoethylidene]amino]oxy] acetic acid and a process useful in the preparation of such salts are disclosed herein.

2 Claims, No Drawings

[3S(Z)]-2-[[[1-(2-AMINO-4-THIAZOLYL)-2-[[2,2-DIMETHYL-4-OXO-1-(SULFOOXY)-3-AZETIDINYL]AMINO]-2-OXOETHYLIDENE]-AMINO]OXY] ACETIC ACID AND INTERMEDIATE

BACKGROUND OF THE INVENTION

U.S. Pat. No. 4,337,197, issued June 29, 1982 describes O-sulfated β-lactam hydroxamic acids having antibacterial activity. Preferred compounds, as disclosed by the patent, have the formula

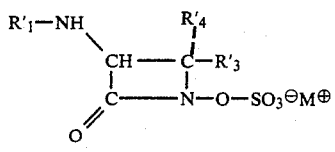

wherein $R'_1$ is acyl, $R'_3$ and $R'_4$ are the same or different and each is hydrogen or alkyl, and $M^\oplus$ is hydrogen or a cation.

Several processes for preparing the above compounds are described including a process which utilizes an intermediate having the formula

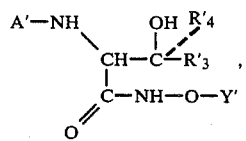

wherein A' is a nitrogen protecting group and Y' is benzyl or pivaloyl. As described in the patent, the hydroxyl group of the above intermediate is converted to a leaving group, using, for example, a classical reagent such as methanesulfonyl chloride. The fully protected compound has the formula

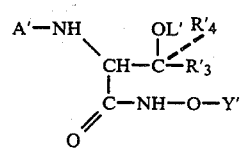

(L' is a leaving group), and can be cyclized by treatment with base, e.g., potassium carbonate, to yield a compound having the formula

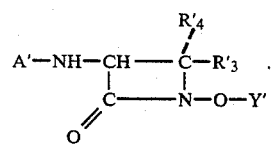

Alternatively, the patent describes the single step cyclization process which comprises treatment of an intermediate having the formula

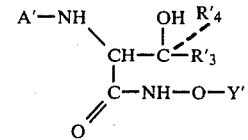

with triphenylphosphine and diethylazodicarboxylate.

BRIEF DESCRIPTION OF THE INVENTION

It has been found that a pharmaceutically acceptable salt of [3S(Z)]-2-[[[1-(2-amino-4-thiazolyl)-2-[[2,2-dimethyl-4-oxo-1-(Sulfooxy)-3-azetidinyl]amino]-2-oxoethylidene]amino]oxy]acetic acid, the compound having the formula

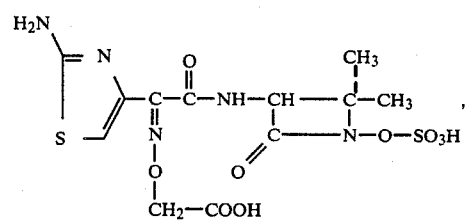

is a superior antibacterial agent.

To prepare [3S(Z)]-2-[[[2-(2-amino-4-thiazolyl)-2-[[2,2-dimethyl-4-oxo-1-(sulfooxy)-3-azetidinyl]amino]-2-oxoethylidene]amino]oxy]acetic acid, it was desirable to improve upon the process described in U.S. Pat. No. 4,337,197, and set forth above in the Background of the Invention. It has been found that a compound having the formula

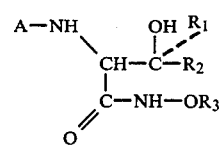

can be sulfonated to yield a compound having the formula

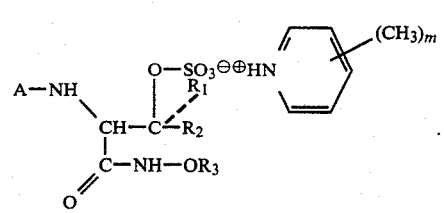

Compounds of formula III are novel intermediates, and as such, they form an integral part of this invention. Cyclization of a fully protected compound of formula III yields the useful intermediate having the formula

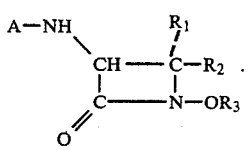

As used in formulas II, III and IV, and throughout the specification, the symbols are as defined below.

A is benzyloxycarbonyl, p-nitrobenzyloxycarbonyl, t-butyloxycarbonyl, o-nitrophenylsulfenyl or triphenylmethyl;

$R_1$ and $R_2$ are the same or different and each is alkyl of 1 to 4 carbons;

$R_3$ is benzyl, p-nitrobenzyl, benzyloxymethyl, 2-methoxy-2-propyl, 2-ethoxy-2-propyl, tetrahydropyran-2-yl, 2-trimethylsilylethyl, t-butyldimethylsilyl, or t-butyldiphenylsilyl;

The pharmaceutically acceptable salts of the compounds of formula I include those basic salts formed with inorganic and organic cations. Such salts include ammonium salts, alkali metal salts such as sodium and potassium salts, alkaline earth metal salts such as calcium and magnesium salts and salts derived from organic bases such as dicyclohexylamine, benzathine, hydrabamine, N-methyl-D-glucamine.

The compounds of formulas I, VI, and IX are pictured as acids. They can also exist, however, as zwitterions (internal or inner salts), and these are also included within the language "pharmaceutically acceptable salts" and the scope of this invention.

DETAILED DESCRIPTION OF THE INVENTION

Pharmaceutically acceptable salts of [3S(Z)]-2-[[[1-(2-amino-4-thiazolyl)-2-[[2,2-dimethyl-4-oxo-1-(sulfooxy)-3-azetidinyl]amino]-2-oxoethylidene]amino]oxy]acetic acid are unexpectedly superior antibacterial agents compared to other O-sulfated β-lactam hydroxamic acids. More specifically, the salts of this invention have superior oral adsorption characteristics in a mammalian host, in conjuction with improved stability to β-lactamase enzymes responsible for β-lactam resistance in the clinic and also improved chemical stability.

Pharmaceutically acceptable salts of the compound of formula I can be used to combat gram-negative bacterial infections in mammalian species, such as domesticated animals (e.g., dogs, cats, horses and the like) and humans. The salts are particularly suitable for oral administration, but all modes of administration which have been used in the past to deliver penicillins and cephalosporins to the site of the infection are also contemplated.

For combating a gram-negative bacterial infection in a mammalian host, a pharmaceutically acceptable salt of the compound of formula I can be administered to a mammal in need thereof in an amount of about 1 mg/kg/day to about 350 mg/kg/day, preferably about 10 mg/kg/day to about 100 mg/kg/day.

For oral administration, a pharmaceutically acceptable salt of the compound of formula I can be formulated as a tablet, capsule, or solution or suspension in an aqueous vehicle.

Pharmaceutically acceptable salts of [3S(Z)]-2-[[[1-(2-amino-4-thiazolyl)-2-[[2,2-dimethyl-4-oxo-1-(sulfooxy)-3-azetidinyl]amino]-2-oxoethylidene]amino]oxy]acetic acid can be prepared following the methodology described in U.S. Pat. No. 4,337,197, issued June 29, 1982 (utilizing the intermediates described above in the Background of the Invention). This process has been improved.

Conversion of the hydroxyl group of a compound having the formula

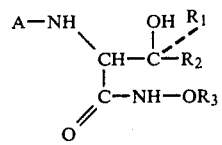

to a leaving group is complicated by the fact that the compound is a tertiary alcohol. It has been found that if a compound of formula II is sulfonated using a pyridine (or substituted pyridine) sulfur trioxide complex having the formula

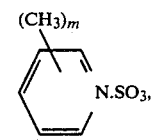

wherein m is 0, 1, 2 or 3, the reaction will give a compound having the formula

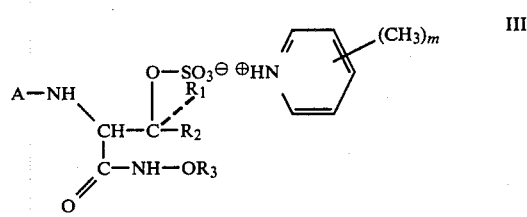

in high yield. The pyridine-sulfur trioxide complex reacts preferentially with the hydroxyl group (as desired).

The sulfonation reaction can be run in an organic solvent such as pyridine, mono-, di- or trimethylpyridine, chlorinated hydrocarbons (e.g., dichloromethane, 1,2-dichloroethane), acetonitrile, dimethylformamide and dioxane. The reaction will preferably be run at about 0°–100° C.

Base mediated cyclization of a compound of formula III yields the corresponding intermediate having the formula

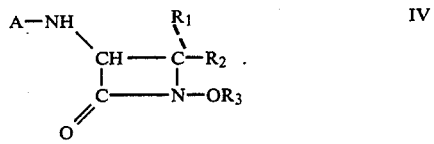

The base is preferably an inorganic base such as an alkali metal carbonate (e.g., sodium carbonate or potassium carbonate) and should be present in excess (about 2 to 10 equivalents per reactant of formula III). The reaction is preferably run in an aqueous organic solvent mixture. The organic component can be ethyl acetate, acetonitrile, acetone, methyl ethyl ketone, methyl propyl ketone, methyl butyl ketone, methyl isobutyl ketone, 1,2-dichloroethane, pyridine, or mono-, di- or trimethylpyridine.

An intermediate of formula IV can be used to prepare an antibacterial agent which is a salt of a compound having the formula

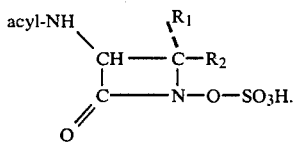

As described in U.S. Pat. No. 4,337,197, the protecting group "$R_3$" can first be removed from an intermediate of formula IV to yield the corresponding hydroxamic acid having the formula

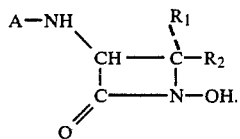

The reactions used to remove the various "$R_3$" groups are known in the art and will, of course, depend on the particular "$R_3$" group.

Sulfonation of a compound of formula VII yields the corresponding compound having the formula

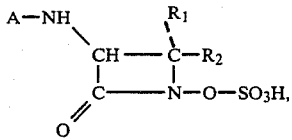

or a basic salt thereof, and can be accomplished by reaction with a complex of sulfur trioxide with pyridine, dimethylformamide or 2,6-lutidine.

Removal of the 3-amino protecting group "A" from a compound of formula VIII yields the corresponding key intermediate having the formula

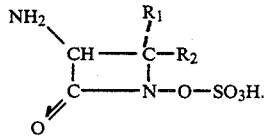

The procedure used for the removal of the protecting group will depend on the particular protecting group.

Acylation of an intermediate of formula IX using art-recognized techniques yields an antibacterial agent of formula VI. For example, the acylation can be accomplished using a carboxylic acid, carboxylic acid halide or carboxylic acid anhydride.

The following examples further illustrate the process of this invention. The process is used to prepare [3S(Z)]-2-[[[1-(2-amino-4-thiazolyl)-2-[[2,2-dimethyl-4-oxo-1-(sulfooxy)-3-azetidinyl]amino]-2-oxoethylidene]amino]oxy] acetic acid as a chiral material and as a component of a racemic mixture.

EXAMPLE 1

[3±(Z)]-2-[[[1-(2-Amino-4-thiazolyl)-2-[[2,2-dimethyl-4-oxo-1-(sulfooxy)-3-azetidinyl]amino]-2-oxoethylidene]amino]oxy]acetic acid, disodium salt (A) N-(t-Butyloxycarbonyl)-N²-(phenylmethoxy)-D,L-3-hydroxyvalinamide A solution of 24.84 g (106.6 mmol) of N-t-butyloxycarbonyl-D,L-3-hydroxyvaline and 16.33 g (106.6 mmol) of hydroxybenzotriazole monohydrate in 500 ml of dry tetrahydrofuran was cooled to −10° C. and 22 g (106.6 mmol) of dicyclohexylcarbodiimide was added. The mixture was stirred under nitrogen for 1 hour at 0° C. Subsequently, a solution of 13.13 g (106.6 mmol) of 0-benzylhydroxylamine in 250 ml of dry tetrahydrofuran was added over 15 minutes to the activated ester mixture, and the resultant mixture was stirred under nitrogen for 1 hour at 0° C. The insoluble material was filtered away, and the filtrate was stripped to a foam in vacuo. The foam was extracted with ethyl acetate and more insoluble material was removed by filtration. The filtrate was washed two times with 5% sodium bicarbonate solution. The organic phase was dried (sodium sulfate) and evaporated to a syrup, which was crystallized from 130 ml of isopropyl ether to give 24.7 g of the title compound, melting point 76°-78° C. The mother liquor was evaporated to a syrup (10 g), which was chromatographed on a column containing 300 g of SilicAR CC-4 packed in chloroform. The column was eluted first with 1 liter of chloroform and then with 2 liters of 2% methanol in chloroform. The latter solvent system eluted additional product (TLC $R_f$ 0.9, chloroform/methanol, 3:1) plus an impurity that moved to the solvent front. Pooled fractions were evaporated in vacuo to a syrup (8 g), which was crystallized from 25 ml of isopropyl ether to afford another 5 g of the title compound, melting point 76°-78° C.

(B)
N-(t-Butyloxycarbonyl)-N²-(phenylmethoxy)-D,L-3-(sulfooxy)valinamide, pyridinium salt Dry pyridine (8.08 ml, 0.10 mole) was placed in a 500 ml round bottom flask and cooled to −10° C. under nitrogen. Trimethylsilyl chlorosulfonate (15.6 ml, 0.10 mole) was added dropwise (vigorous magnetic stirring) after which the very thick reaction mixture (due to product precipitation) was stirred for 0.5 hours at 0° C. Chlorotrimethylsilane was removed in vacuo yielding 15 g of pyridine-sulfur trioxide complex.

N-(t-Butyloxycarbonyl)-N²-(phenylmethoxy)-D,L-3-hydroxyvalinamide (16.92 g, 50 mmol) was dissolved in 200 ml of dry pyridine, and 9.87 g (62.5 mmol) of pyridine-sulfur trioxide complex was added. The mixture was stirred at 55° C. under nitrogen for 2 hours. Another portion (790 mg, 5 mmol) of pyridine-sulfur trioxide complex was added and stirring was continued 1 hour longer. TLC (n-butanol/acetic acid/water (3:1:1)) showed only one product, $R_f$ 0.77 (starting material moves to solvent front). The reaction mixture was stripped in vacuo to an oil. The oil was stripped from acetonitrile three times in vacuo to give crude title compound as a foam. The yield was assumed to be quantitative.

(C)
(3±)-3-[(t-Butyloxycarbonyl)amino]-4,4-dimethyl-1-(phenylmethoxy)-2-azetidinone The flask containing crude N-(t-butyloxycarbonyl)-N²-(phenylmethoxy)-D,L-3-(sulfooxy)valinamide, pyridinium salt (ca. 50 mmol) was placed in an ice bath and 400 ml of ethyl acetate, followed by a solution of 42.8 g (0.31 mole) of potassium carbonate in 90 ml of water, was added with vigorous stirring. The resultant mixture was stirred vigorously under reflux (oil bath temperature 95° C.) for 2 hours under nitrogen. The reaction mixture was cooled to room temperature and the phases were separated. The aqueous phase was extracted with 2×200 ml of ethyl acetate and all organic phases were combined, dried (sodium sulfate) and evaporated in vacuo. The oil was taken into 40% ethyl acetate/hexane (125 ml) and filtered rapidly through a 350 ml pad (10 cm) of silicAR CC-7 using 3-4 liters of 40% ethyl acetate/hexane. The filtrate was evaporated in vacuo to a solid (12.2 g). Crystallization from 50 ml of isopropyl ether gave 7.15 g of the title compound, melting point 110° C. Evaporation of the mother liquor gave 4.75 g of gummy solid containing ca. 15% additional compound on the basis of the $^1$H nmr spectrum.

(D)

(3±)-3-[(t-Butyloxycarbonyl)amino]-1-hydroxy-4,4-dimethyl-2-azetidinone (3±)-3-[(t-Butyloxycarbonyl)amino]-4,4-dimethyl-1-(phenylmethoxy)-2-azetidinone (8.07 g, 25 mmol) was hydrogenated at atmospheric pressure and ambient temperature in 40 ml of methanol with 0.6 g of 10% palladium on charcoal as catalyst for 2 hours. The reaction mixture was filtered through a pad of Celite and the filtrate was concentrated in vacuo. Acetonitrile was added and evaporated from the residue (twice) to yield 5.78 g of the title compound as a solid foam.

(E)

(3±)-3-[(t-Butyloxycarbonyl)amino]-2-oxo-4,4-dimethyl-1-azetidinylsulfate, potassium salt Pyridine. SO$_3$ complex (8.02 g, 50 mmole) was added portionwise to a solution of (3±)-3-[(t-butyloxycarbonyl)amino]-1-hydroxy-4,4-dimethyl-2-azetidinone (5.78 g, 25 mmole) in dry pyridine (120 ml) at 0° C. under argon. The reaction mixture was stirred at room temperature for 2.5 hours and concentrated in vacuo. The residue was dissolved in 32 ml of a 10% acetone:.5 M monobasic potassium phosphate aqueous buffer (pH 7) solution, and the pH was adjusted to 5.2 with 1N potassium hydroxide. This was chromatographed through 270 ml of Dowex-50 (K+) resin with a 10% acetone:water solution. The appropriate fractions were combined and concentrated in vacuo to yield 13.6 g of crude product. This was further purified by chromatography through 680 ml of HP-20 resin first with 200 ml of water, then with 10% acetone:water. The appropriate fractions were combined and lyophilized to yield 7.13 g of the title compound, melting point 163°-170° C., dec.

(F)

(3±)-3-Amino-2-oxo-4,4-dimethyl-1-azetidinylsulfate (3±)-3-[(t-Butyloxycarbonyl)amino]-4,4-dimethyl-1-azetidinylsulfate, potassium salt (5.48 g, 15 mmole) was suspended in 20 ml of dry dichloromethane at −10° C. under argon. Anisole (6 ml) was added followed by the addition of 26 ml of trifluoroacetic acid over 2 minutes. The reaction mixture was stirred at −10° C. for 20 minutes and then concentrated in vacuo. The residue was triturated with ether (three times) and dried in vacuo to give crude title compound as a white solid.

(G)

[3±(Z)]-2-[[[1-(2-Amino-4-thiazolyl)-2-[[2,2-dimethyl-4-oxo-1-(sulfooxy)-3-azetidinyl]amino]-2oxoethylidene]amino]oxy]acetic acid, diphenylmethyl ester, sodium salt (Z)-(2-Amino-4-thiazolyl)[[(2-diphenylmethoxy)-2-oxoethoxy]imino]acetic acid (6.52 g, 16 mmole) and triethylamine (2.5 ml, 18 mmole) were dissolved in 60 ml of dimethylformamide at −30° C. under argon. Diphenyl chlorophosphate (3.5 ml, 17 mmole) was added dropwise and the reaction mixture was stirred at −30° C. for 1.5 hours.

To the crude (3±)-3-amino-2-oxo-4,4-dimethyl-1-azetidinylsulfate prepared above, dissolved in 10 ml of dimethylformamide at 0° C., was added 6.6 ml of triethylamine. This solution was added dropwise to the above mixed anhydride at −30° C. The reaction mixture was stirred at −30° to −20° C. for 3.5 hours, and allowed to come to room temperature. Insolubles were filtered off, and the filtrate was concentrated in vacuo. The residue was dissolved in 60 ml of a 20% acetone:.5 M monobasic sodium phosphate buffer (pH 7) and the pH was adjusted to 6.0 with 2N sodium hydroxide. This was chromatographed through 300 ml of Dowex 50 Na+ resin with 20% acetone:water solution. The appropriate fractions were combined and lyophilized to dryness. The crude product was dissolved in 200 ml of wet acetonitrile and the insoluble inorganic salts were removed by filtration. The filtrate was concentrated in vacuo to yield 19.32 g of the title compound, contaminated with the acid starting material.

(H)

[3±(Z)]-2-[[[1-(2-Amino-4-thiazolyl)-2-[[2,2-dimethyl-4-oxo-1-(sulfooxy)-3-azetidinyl]amino]-2-oxoethylidene]amino]oxy]acetic acid, disodium salt Crude [3±(Z)]-2-[[[1-(2-amino-4-thiazolyl)-2-[[2,2-dimethyl-4-oxo-1-(sulfooxy)-3-azetidinyl]amino]-2-oxoethylidene]amino]oxy]acetic acid, diphenylmethyl ester, sodium salt (19.3 g) was suspended in 50 ml of dichloromethane and 6 ml of anisole at −10° C. under argon. Trifluoroacetic acid (90 ml) was added, and the reaction mixture was stirred for 1 hour, concentrated in vacuo, and triturated with ether (three times). The crude product was dissolved in 40 ml of 0.5M monobasic sodium phosphate pH 7.0 buffer and the pH was adjusted to 6.8 with 2N sodium hydroxide. This solution was chromatographed through 900 ml of HP-20 with water. The appropriate fractions were divided into two portions. The less pure portion was rechromatographed on 500 ml of HP-20. The appropriate fractions were combined with those of the first chromatography and lyophilized to yield 3.8 g of the title compound, melting point 195°-210° C., dec.

Analysis Calc'd. for $C_{12}H_{13}N_5O_9S_2Na_2.2.4\ H_2O$: C, 27.46; H, 3.41; N, 13.35; S, 12.22. Found: C, 27.46; H, 3.48; N, 13.06; S, 12.04.

EXAMPLE 2

[3S(Z)]-[[[1-(2-Amino-4-thiazolyl)-2-[[2,2-dimethyl-4-oxo-1-(sulfooxy)-3-azetidinyl]amino]-2oxoethylidene]amino]oxyacetic acid, disodium salt (A) N-(t-Butyloxycarbonyl)-L-3-hydroxyvaline, α-methylbenzylamine salt A solution of N-t-butyloxycarbonyl-β-hydroxyvaline (7.02 g, 30 mmoles) in 250 ml of ethyl ether was treated with 3.63 g (30 mmoles) of S-(−)-α-methyl benzylamine and the resultant solution seeded with finely divided salt from a previous resolution. After standing 8 hours at 25° C. the resulting white solid was filtered, washed with ether and dried in air to give 4.78 g of crude title compound, melting point 137°-140° C.

Recrystallization of 8.87 g of crude material was accomplished by dissolving in 200 ml of acetonitrile at reflux and cooling to 25° C. Standing at 25° C. for 1 hour and filtering gave, after washing with acetonitrile and ethyl acetate, and drying in air, 6.81 g of the title compound, melting point 144°–146° C. A second recrystallization of the 6.81 sample from 150 ml of acetonitrile gave 6.02 g of title compound, melting point 146°–147° C. $[\alpha]_D = -4.5°$ (C=2.0, methanol).

(B) N-(t-Butyloxycarbonyl)-L-3-hydroxyvaline

N-(t-Butyloxycarbonyl)-L-3-hydroxyvaline, α-methylbenzylamine salt (6.02 g, 17.0 mmoles) was shaken with a mixture of 250 ml of ethyl acetate and 100 ml of 10% potassium bisulfate and the layers separated. The organic layer was washed with water and brine, dried (sodium sulfate) and evaporated to a foam. Trituration with hexane gave the title compound as a free flowing white powder, 3.79 g melting point 116°–118° C., $[\alpha]_D = +7.6°$ C. (C=2.0, ethyl acetate).

A sample of the title compound was converted to its methyl ester with diazomethane. Proton NMR (400 MHz) of a mixture of 5 mg of the methyl ester and 10 mg of tris[3-(heptafluoropropylhydroxymethylene)-d-camphorato], europium (III) at 0° C. showed a 95:5 ratio of enantiomers.

Deprotection of the compound (hydrochloric acid/ethyl acetate) to its free amino acid hydrochloride and comparison to the literature rotation indicated the absolute stereochemistry of the compound to be S (see *Bull. Chem. Soc. Japan*, 39, 2287(1966)).

(C) N-(t-Butyloxycarbonyl)-$N^2$-(phenylmethoxy)-L-3-hydroxyvalinamide

Following the procedure of example 1A, but substituting N-(t-butyloxycarbonyl)-L-3hydroxyvaline for N-(t-butyloxycarbonyl)-D,L-3hydroxyvaline yielded the title compound.

(D) (3S)-3-[(t-Butyloxycarbonyl)amino]-4,4-dimethyl-1-(phenylmethoxy)-2-azetidinone Following the procedures of example 1B and 1C, but substituting N-(t-butyloxycarbonyl)-$N^2$-(phenylmethoxy)-L-3-hydroxyvalinamide for N-(t-butyloxycarbonyl)-$N^2$-(phenylmethoxy)-D,L-3hydroxyvalinamide yielded the title compound. The mother liquor from the crystallization was purified by flash chromatography on LPS-1 silica gel (eluting with 20% ethyl acetate/hexane).

(E) (3S)-3-[(t-Butyloxycarbonyl)amino]-1-hydroxy-4,4-dimethyl-2-azetidinone

Following the procedure of example 1D, but substituting (3S)-3-[(t-butyloxycarbonyl)amino]-4, 4-dimethyl-1-(phenylmethoxy)-2-azetidinone for (3±)-3-[(t-butyloxycarbonyl)amino]-4,4-dimethyl-1-1-(phenylmethoxy)-2-azetidinone yielded the title compound.

(F) (3S)-3-[(t-Butyloxycarbonyl)amino]-2-oxo-4,4-dimethyl-1-azetidinylsulfate, potassium salt Following the procedure of example 1E, but substituting (3S)-3-[(t-butyloxycarbonyl)amino]-1-hydroxy-4,4-dimethyl-2-azetidinone for (3±)-3-[(t-butyloxycarbonyl)amino]-1-hydroxy-4,4-dimethyl-2-azetidinone yielded the title compound. After removing the volatiles, the crude residue was dissolved in 10% acetone/0.5M monobasic potassium phosphate buffer (pH7.2) and the pH was adjusted to 5.0 with 3N potassium hydroxide. This solution was subjected to chromatography on Dowex (potassium form) followed by purification on HP-20.

(G) [3S(Z)]-2-[[[1-(2-Amino-4-thiazolyl)-2-[[2,2-dimethyl-4-oxo-1-(sulfooxy)-3-azetidinyl]amino]-2oxoethylidene]amino]oxy]acetic acid, diphenylmethyl ester, sodium salt Diisopropylethylamine (0.54 ml, 3.09 mmoles) was added to 1.152 g (2.81 mmoles) of (Z)-(2-amino-4-thiazolyl)[[2-diphenylmethoxy-2-oxoethoxy]imino]acetic acid in 9.4 ml of dimethylformamide. The mixture was cooled to −20° C., diphenylchlorophosphate (0.59 ml, 2.81 mmoles) was added, and the resulting mixture was stirred for 1 hour to yield a mixed anhydride.

(3S)-3-[(t-Butyloxycarbonyl)amino]-2-oxo-4,4-dimethyl-1-azetidinylsulfate, potassium salt (0.98 g, 2.81 mmoles) was suspended in 7.5 ml of dichloromethane, and cooled to −10° C. Anisole (2.13 ml) was added and then 9.4 ml of trifluoroacetic acid was added. The resulting mixture was stirred at −10° C. for 1 hour. Toluene (~5 ml) was added, and the volatiles were evaporated. The residue was triturated with hexane and anhydrous ether and evacuated to yield a white powder, (3S)-amino-2-oxo-4,4-dimethyl-1-azetidinylsulfate.

The residue was cooled to −20° C. and dissolved in 9.4 ml of dimethylformamide. Diisopropylethylamine (1.47 ml, 8.34 mmoles) was added and then the mixed anhydride was immediately added. The reaction mixture was stirred at −20° C. for 3 hours. The volatiles were removed under vacuum, the residue was dissolved in 20% acetone/water at 0° C., and the pH was adjusted to 6.5 with aqueous sodium bicarbonate.

The resulting mixture was purified by column chromatography with 20% acetone/water on Dowex 50×2-400 resin (sodium form), followed by chromatography on HP-20 (eluting with water, 5% acetone/water, 10% acetone/water, 20% acetone/water, 30% acetone/water, and 40% acetone/water) to give the title compound.

(H) [3S(Z)]-2-[[[1-(2-Amino-4-thiazolyl)-2-[[2,2-dimethyl-4-oxo-1-(sulfooxy)-3-azetidinyl]amino]-2-oxoethylidene]amino]oxy]acetic acid, disodium salt

[3S(Z)]-2-[[[1-(2-Amino-4-thiazolyl)-2-[[2,2-dimethyl-4-oxo-1-(sulfooxy)-3-azetidinyl]amino]-2oxoethylidene]amino]oxy]acetic acid, diphenylmethyl ester, sodium salt was suspended in 11.2 ml of dichloromethane at −10° C. Anisole (1.12 ml) was added, followed by the dropwise addition of 18.7 ml of trifluoroacetic acid. The mixture was stirred at 0° C. for 40 minutes. Toluene was added, and the volatiles were evaporated. The residue was triturated with anhydrous ether and evacuated to yield a white solid. The residue was dissolved in water (pH 2.75) and purified by chromatography on HP-20 (eluting with water, 5% acetone/water, 10% acetone/water, and 20% acetone/water to yield upon lyophilization 640 mg of the zwitterion of the title compound. The zwitterion was dissolved in water, and 2 equivalents of sodium bicarbonate (244 mg, 2.9 mmoles) were added (pH=5.75). Chromatography of this solution on HP-20 (eluting with water) yielded upon lyophilization 572 mg of the title compound, melting point 140°–145° C., dec.

Analysis calc'd. for $C_{12}H_{13}N_5O_9S_2Na_2 \cdot 1.56H_2O$: C, 28.31; H, 3.10; N, 13.64. Found: C, 28.31; H, 3.19; N, 13.76.

What is claimed is:

1. The inner salt or a pharmaceutically acceptable basic salt of [3S(Z)]-2-[[[1-(2-amino-4-thiazolyl)-2-[[(2,2-dimethyl-4-oxo-1-(sulfooxy)-3-azetidinyl]amino]-2oxoethylidene]amino]oxy] acetic acid.

2. The compound (3S)-3-amino-2-oxo-4,4-dimethyl-1-azetidinylsulfate or a basic salt thereof.

* * * * *